United States Patent
Lebrun et al.

(10) Patent No.: US 11,324,399 B2
(45) Date of Patent: May 10, 2022

(54) METHOD AND SYSTEM FOR DETERMINING A PUPILLARY DISTANCE OF AN INDIVIDUAL

(71) Applicant: Essilor International, Charenton-le-Pont (FR)

(72) Inventors: Charles Lebrun, Charenton-le-Pont (FR); Cécile Petignaud, Charenton-le-Pont (FR); Alvin François, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 226 days.

(21) Appl. No.: 16/622,403

(22) PCT Filed: Jun. 15, 2018

(86) PCT No.: PCT/EP2018/066008
§ 371 (c)(1),
(2) Date: Dec. 13, 2019

(87) PCT Pub. No.: WO2018/229273
PCT Pub. Date: Dec. 20, 2018

(65) Prior Publication Data
US 2020/0196860 A1 Jun. 25, 2020

(30) Foreign Application Priority Data
Jun. 16, 2017 (EP) .................................... 17176501

(51) Int. Cl.
*A61B 3/11* (2006.01)
*A61B 3/00* (2006.01)
*A61B 3/14* (2006.01)

(52) U.S. Cl.
CPC ............ *A61B 3/111* (2013.01); *A61B 3/0041* (2013.01); *A61B 3/145* (2013.01)

(58) Field of Classification Search
CPC ........ A61B 3/111; A61B 3/0041; A61B 3/145
(Continued)

(56) References Cited

U.S. PATENT DOCUMENTS 4,131,338 A * 12/1978 Zalewski ................ A61B 3/111
351/204
6,762,794 B1 * 7/2004 Ogino .................. H04N 13/257
348/262

(Continued)

FOREIGN PATENT DOCUMENTS

| CN | 102439627 A | 5/2012 |
| CN | 103384848 A | 11/2013 |

(Continued)

OTHER PUBLICATIONS

International Search Report and Written Opinion, dated Sep. 17, 2018, from corresponding PCT application No. PCT/EP2018/066008.

(Continued)

*Primary Examiner* — Mohammed A Hasan
(74) *Attorney, Agent, or Firm* — Nixon & Vanderhye

(57) ABSTRACT

A method for determining a pupillary distance of an individual, includes the following steps: —displaying an object on a screen located in front of the individual, the displayed object being positioned at a location in front of one eye of the individual; —instructing the individual to look with at least the eye at the displayed object; —acquiring at least an image of a part of the body of the individual including the eye; —determining the location of a plurality of specific features in the acquired image, one of the specific features being a pupil of the eye of the individual; and —calculating the pupillary distance based on the location of the plurality of specific features. A corresponding system is also described.

14 Claims, 4 Drawing Sheets

Figure 1:
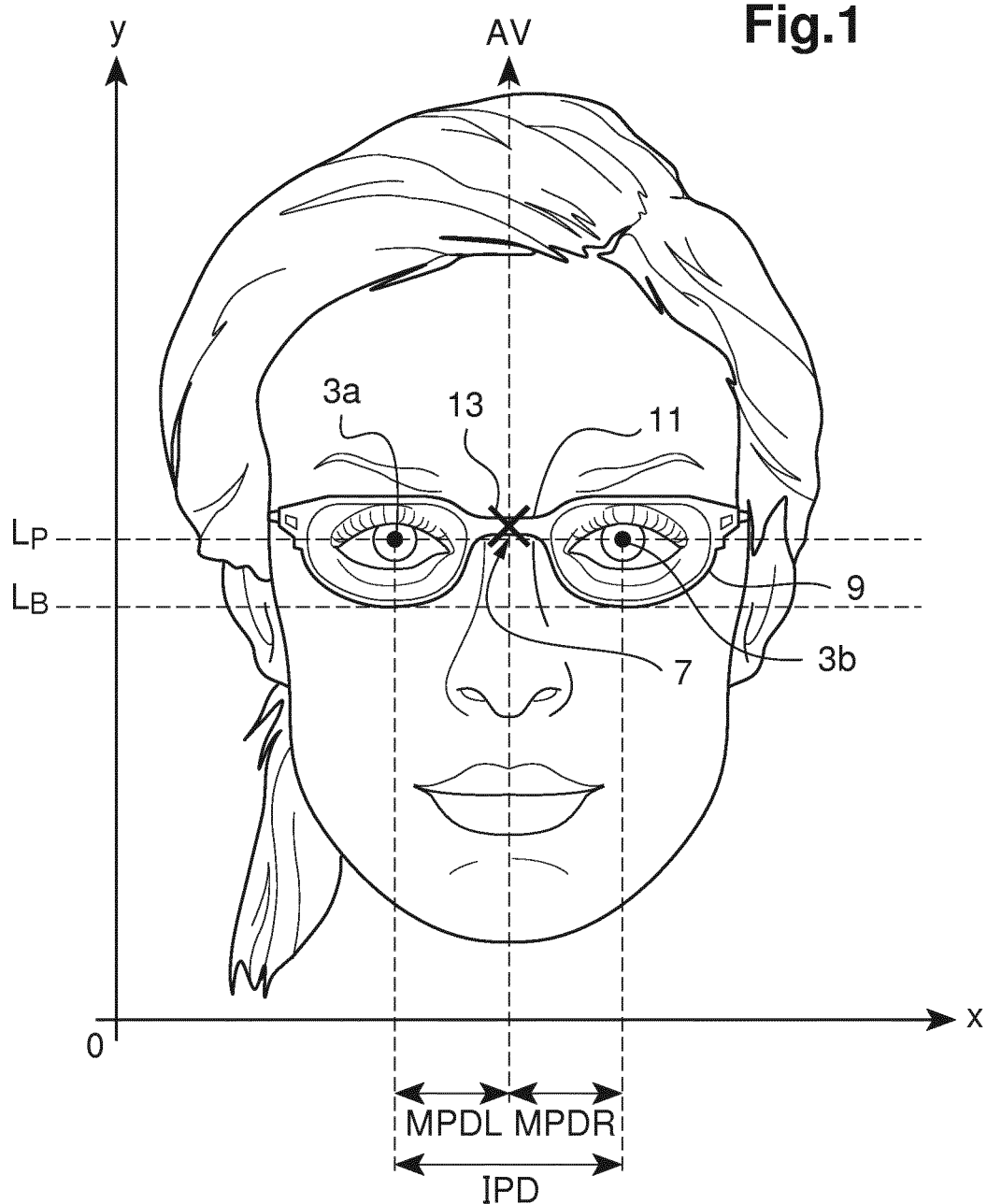

(58) Field of Classification Search
USPC .......................................................... 351/204
See application file for complete search history.

(56) References Cited

U.S. PATENT DOCUMENTS

| | | |
|---|---|---|
| 2010/0220285 A1 | 9/2010 | Simmonds |
| 2012/0050516 A1 | 3/2012 | Tsukizawa et al. |
| 2013/0188128 A1 | 7/2013 | Divo et al. |
| 2013/0314668 A1 | 11/2013 | Haddadi et al. |
| 2016/0124249 A1 | 5/2016 | Haddadi et al. |
| 2016/0299360 A1* | 10/2016 | Fonte ................. G06Q 30/0621 |
| 2017/0168323 A1 | 6/2017 | Gardner |

FOREIGN PATENT DOCUMENTS

| | | |
|---|---|---|
| CN | 105308494 A | 2/2016 |
| EP | 2261857 A1 | 12/2010 |
| WO | 2009/007731 A1 | 1/2009 |

OTHER PUBLICATIONS

Office Action issued in Chinese Patent Application No. 201880039914.5 dated May 31, 2021.

* cited by examiner

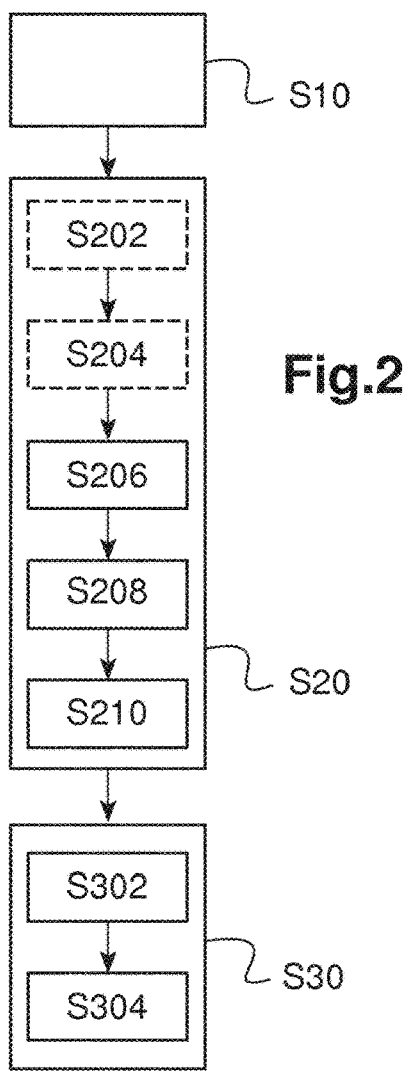
Fig.2
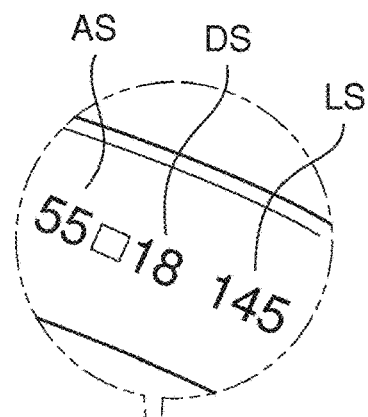
Fig.3
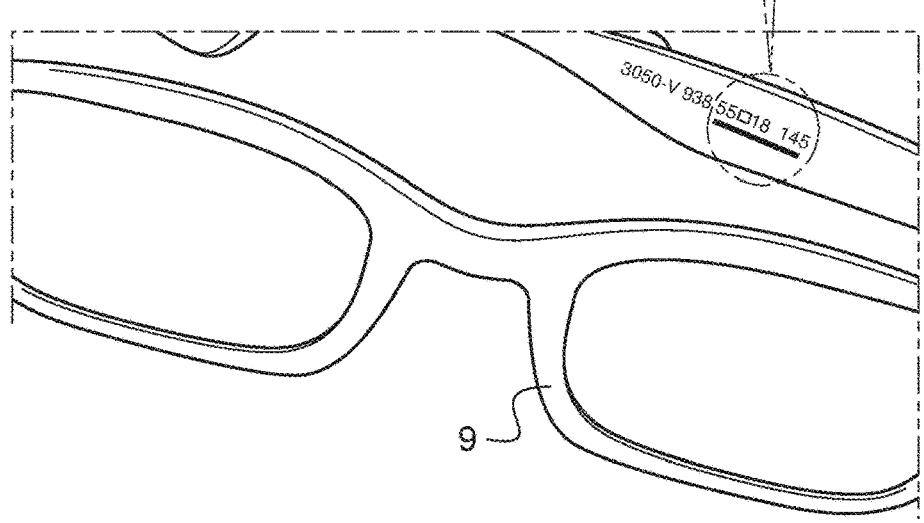

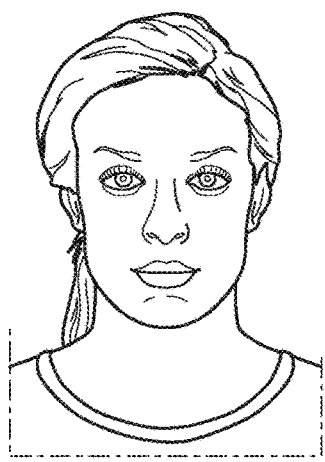
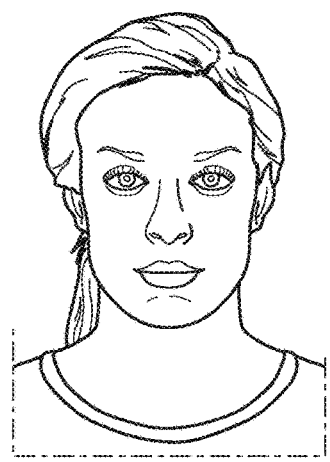
Fig.4a  Fig.4b  Fig.4c
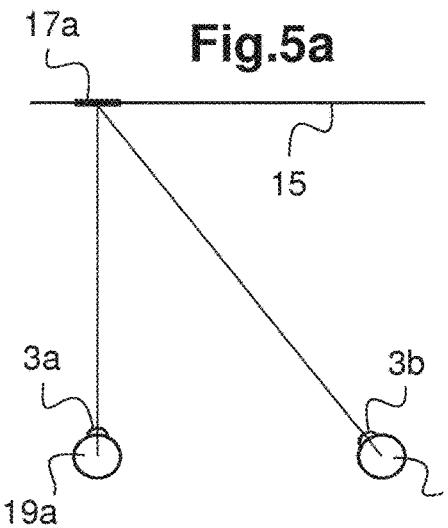
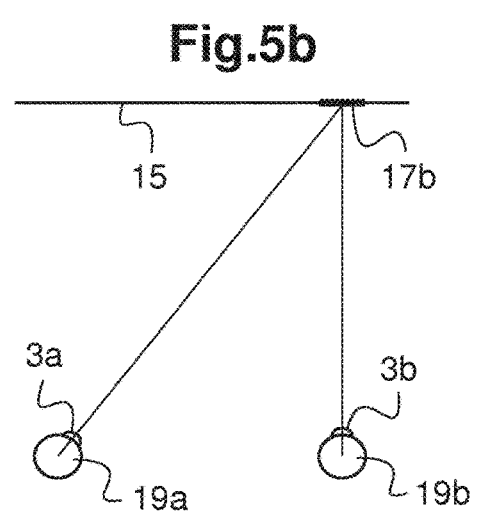
Fig.5a  Fig.5b
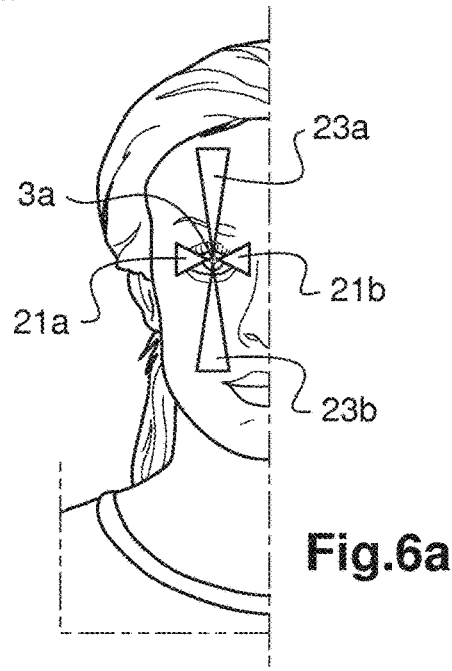
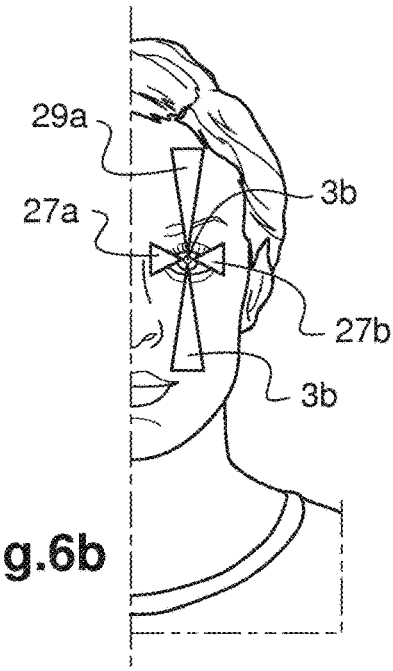
Fig.6a  Fig.6b

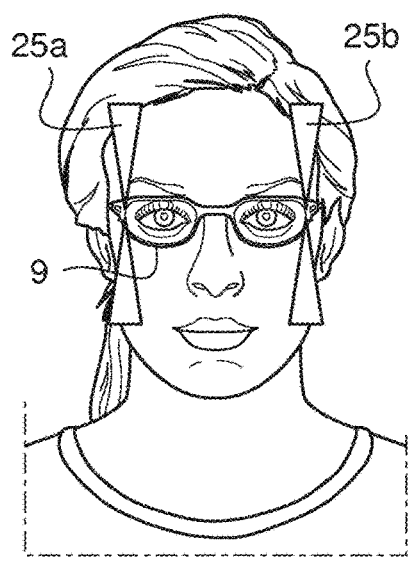
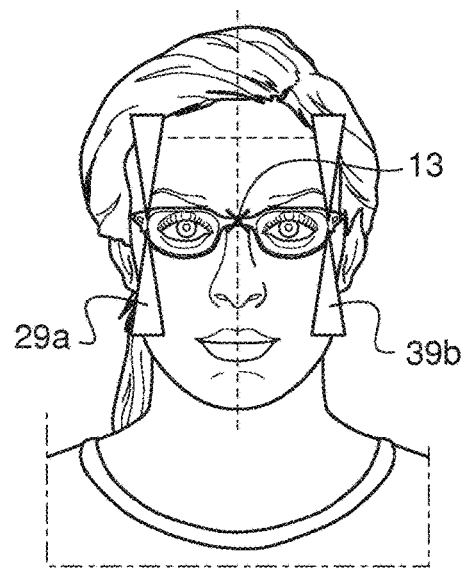
Fig.7a  Fig.7b
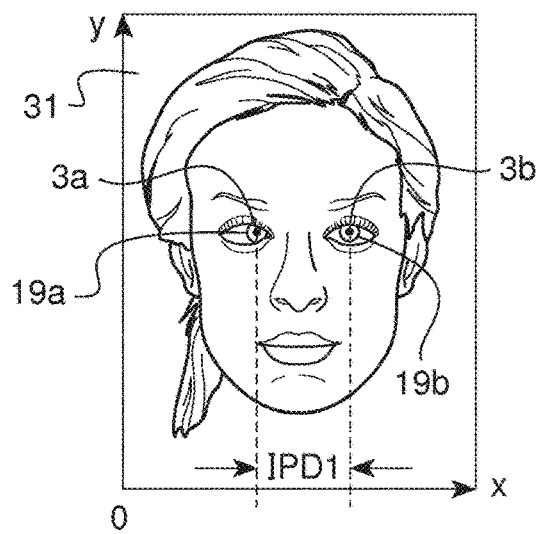
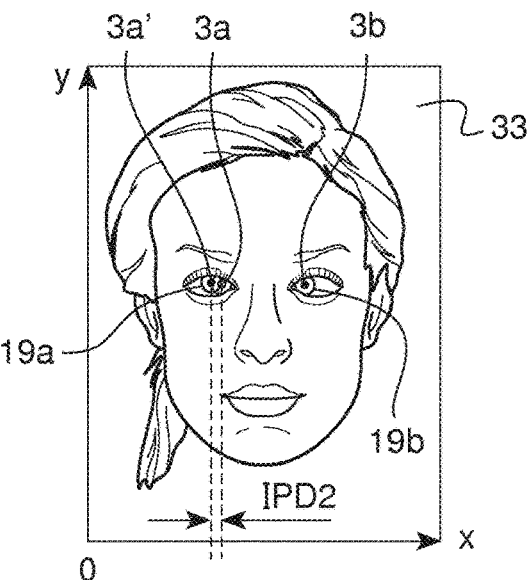
Fig.8a  Fig.8b
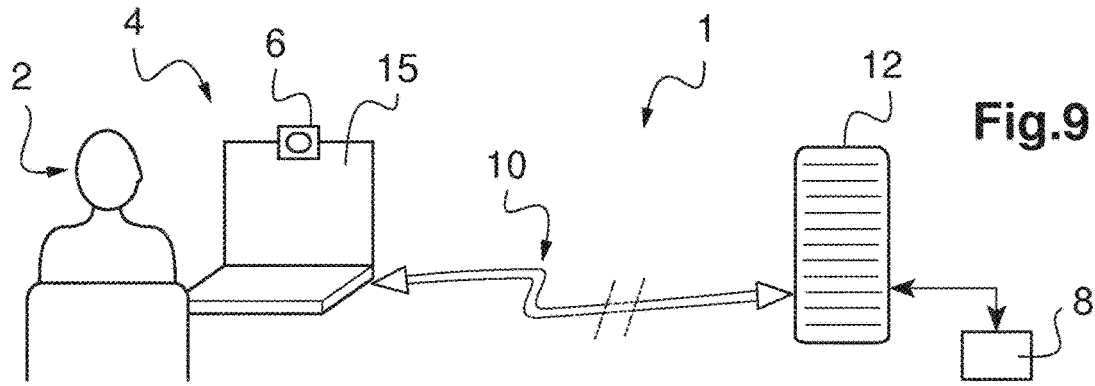
Fig.9

METHOD AND SYSTEM FOR DETERMINING A PUPILLARY DISTANCE OF AN INDIVIDUAL

TECHNICAL FIELD OF THE INVENTION

The invention relates to a method for measuring morpho-geometric parameters of an individual who has to wear spectacles.

More precisely the invention relates to a method and a system for determining a pupillary distance of an individual.

BACKGROUND INFORMATION AND PRIOR ART

The morpho-geometric characteristics of an individual who has to wear spectacles are essential parameters to measure in order to manufacture lenses that are well adapted to the individual. These parameters include inter-pupillary distance, monocular pupillary distance, pantoscopic angle etc. It is important to achieve an accurate measurement of these parameters as errors lead to the manufacture of poorly adapted lenses, which in turn leads to the individual ophthalmic discomfort when wearing his/her spectacles.

Methods and devices achieving accurate measurements by opticians are already known. However, when it comes to online measurements the methods currently in use do not provide satisfying results.

For instance, ideally, the measurement of inter-pupillary distance requires the individual to stand in a natural posture and to look straight ahead at a point located at eye-level, a few meters (for example 5 meters) in front of him/her, or looking to the horizon without visual point. This simulates looking at a point situated at infinity, which is essential for an accurate inter-pupillary distance measurement.

While this is easily achieved by an optician, it is harder to accomplish when the individual has to take his/her own measurements. The current online measuring methods require the individual to look at the camera of his/her computer or tablet. As the computer or tablet is usually situated less than a meter away from the individual, the inter-pupillary distance measured corresponds to an intermediate vision and is shorter than the inter-pupillary distance measured when the individual looks at infinity.

To overcome this error in measurement, the methods of the prior art correct the measurements by using a law that links inter-pupillary distances and near vision convergence. However, that law assumes an average eye curvature radius that does not correspond to each individual eye curvature radius.

Furthermore, the convergence depends on the distance between the eyes of the individual and the object he/she is looking at. This distance can be estimated but not accurately measured.

Hence, the corrected measurements are still not accurate enough to provide the individual with lenses adapted to his/her morpho-geometric characteristics.

In the case of monocular pupillary distance measurements, the error in measurement is even greater. The monocular pupillary distance is the distance between the nasion of the individual and one of his/her pupil. Knowing the monocular pupillary distances of a individual allows to precisely position the lenses with respect to the bridge of the spectacle frame, and thus to correctly align the lenses with each pupil of the individual.

As online spectacles ordering is becoming more popular, the need for accurate online measurements increases.

SUMMARY OF THE INVENTION

In this context the invention provides a method for determining a pupillary distance of an individual, comprising the following steps:
- displaying an object on a screen located in front of the individual, the displayed object being positioned at a location in front of one eye of the individual,
- instructing the individual to look with at least said eye at said displayed object,
- acquiring at least an image of a part of the body of the individual including said eye,
- determining the location of a plurality of specific features in the acquired image, one of the specific features being a pupil of said eye of the individual,
- calculating the pupillary distance based on the location of the plurality of specific features.

By looking at an object displayed in front of his/her eye, the individual simulates looking at infinity with said eye. The error in the measurement of the pupillary distance is greatly reduced.

Other advantageous and non-limiting features of the method according to the invention include:
- the method comprises one or several of the steps of:
  - displaying another object on the screen at a location in front of the other eye of the individual,
  - instructing the individual to look with at least said other eye at said other displayed object,
  - acquiring at least another image of a part of the body of the individual including said other eye,
  - determining the location of a another pupil of said other eye in the at least other acquired image,
  - calculating another pupillary distance based on the location of said other pupil of said other eye;
  - the method also comprises a step of evaluating a movement of the individual between the step of acquiring the image and the step of acquiring the other image, typically in order to compensate for this movement (as further explained below);
- the pupillary distance is a monocular pupillary distance;
- the plurality of specific features further includes a specific feature chosen among: an individual spectacle frame (e.g. the middle of the bridge of the frame) and the middle of the nasion of the individual (see below for a definition of nasion);
- the method comprises the step of:
- calculating another monocular pupillary distance based on the location of the pupil of the other eye; and/or the step of:
- calculating an inter-pupillary distance by adding the monocular pupillary distance and the other monocular pupillary distance;
- the pupillary distance is an inter-pupillary distance;
- the inter-pupillary distance is calculated based on the location of the pupil of said one eye and on the location of the pupil of the other eye;
- the step of acquiring is carried out by an image acquisition unit attached to the screen;
- the screen is able to provide a real time display of a mirror image of the individual;
- a step of where the individual is instructed to align the mirror image of his/her face with an alignment target displayed on the screen;

the displayed object or other displayed object comprises a real time display of one eye or the other eye of the individual;

the displayed object or other displayed object comprises a predetermined shape or another predetermined shape, each of the shape being positioned respectively at a location in front of an eye of the individual;

the step of instructing further comprises instructing the individual to stay still in front of the acquisition unit during the step of acquiring at least an image or at least another image;

the step of instructing comprises instructing the individual to pivot his/her head while looking at the displayed object or the other displayed object;

the specific features or the other specific features are located by a person;

the specific features or the other specific features are automatically located by an algorithm;

a step of acquiring an image of an object of known dimensions placed close to the head of the individual and a step of determining an extent of said object of known dimension in the acquired image, said extent then being used during the step of calculating the pupillary distance.

The invention also relates to a device for determining a pupillary distance of an individual comprising:

a screen adapted to display an object at a location in front of one eye of the individual, when said screen is located in front of the individual, and to display instructions for the individual to look with said eye at said displayed object, an image acquisition unit adapted to acquire an image of the body of the individual including one eye of the individual, a calculating unit adapted to calculate the pupillary distance of the individual based on the location of specific features located on an acquired image, wherein the specific features include a pupil of said eye of the individual.

Other advantageous and non-limiting features of the system according to the invention include:

the image acquisition unit is attached to the screen;

the calculating unit is remotely located from the image acquisition unit and the screen.

DETAILED DESCRIPTION OF EXAMPLE(S)

The method and system according to the invention will be described next, in reference with the appended drawings.

On the appended drawings:

FIG. 1 is a schematic front view of the face of an individual looking at infinity.

FIG. 2 is a schematic representation of the steps of the method according to the invention, FIG. 3 gives an example of an object used for calibrating the image, FIGS. 4a, 4b, 4c give an example of images acquired for the method, FIGS. 5a and 5b give a graphical representation of steps of the method wherein the individual is instructed to look at objects displayed on a screen, FIGS. 6a and 6b give a graphical representation of steps of the method wherein specific features are located on an image, FIGS. 7a and 7b give a graphical representation of steps of the method wherein further specific features are located on the image, FIGS. 8a and 8b give a graphical representation of steps of another embodiment of the method according to the invention.

FIG. 9 illustrates a system for determining a pupillary distance of an individual according to the invention.

The invention relates to a system 1 for determining a pupillary distance of an individual 2; an example of the system 1 is illustrated in FIG. 9.

In the example described here, this system 1 for determining a pupillary distance of an individual 2 is computer implemented. The computer 4 may include any type of personal computer with a user interface, for example a desktop, a laptop and a smart device, such as a tablet and a smartphone.

The system 1 for determining a pupillary distance comprises:
a screen 15,
an image acquisition unit 6,
a calculating unit 8.

The screen 15 is adapted to display an object at a location in front of one eye of the individual 2, when said screen 15 is located in front of the individual 2, and to display instructions for the individual 2 to look with said eye at said object displayed on the screen 15.

The image acquisition unit 6 is adapted to acquire an image of the body of the individual 2 including one eye of the individual 2.

The image acquisition unit 6 is for example a webcam. In a preferred example, the image acquisition unit 6 is attached to the screen 15. For example modern computers and smart devices are usually equipped with a webcam integrated above the screen 15. Alternatively, an independent acquisition unit 6 may be attached to the screen.

The computer is able to establish a telecommunication link 10 with a server 12, for example the server 12 of an optician. The computer 4 is able to receive instructions from the server 12 and to send images acquired by the image acquisition unit 6 to the server 12.

The calculating unit 8 receives the images acquired by the acquisition unit 6 via the server 12. The calculating unit 8 is able to implement image processing algorithms such as Optical Character Recognition (OCR) algorithms and facial recognition algorithms. The use of these algorithms will be explained in more details thereafter.

The calculating unit 8 is also adapted to calculate the monocular pupillary distances and the inter-pupillary distance of the individual 2 based on the location of specific features located on acquired images, wherein the specific features include a pupil of said eye of the individual 2. The terms monocular pupillary distances and the inter-pupillary distance will be described in more details thereafter.

More specifically, the calculating unit 8 is able to perform some of the steps of the method according to the invention.

The calculating unit 8 is equipped with a memorization unit where it can store a computer program for causing when executed the calculating unit 8 to perform the steps of the method.

The calculating unit 8 is preferably remotely located from the image acquisition unit 6 and the screen 15. For example it is located at an office of an optician.

The calculating unit 8 is able to telecommunicate with the computer 4 of the individual 2 for example through Internet via the server 12.

FIG. 1 illustrates the face of an individual 2 looking straight ahead at infinity. FIG. 1 shows the definitions of a few parameters relative to a spectacle frame and to the head of the individual 2. The image has a coordinate system (x, y) defined by a horizontal axis (0x) and a vertical axis (0y). These two axes (0x), (0y) correspond for example to a horizontal edge and to a vertical edge of the image respectively.

Each pixel of the image has an address in the coordinate system (x, y) of the image.

Dimensions of elements appearing on the image are referred to as "pixel dimensions" and dimension of elements in reality are referred to as "real dimensions".

The method according to the invention allows determining a pupillary distance of an individual 2. Here, we use "pupillary distance" as a general term referring to morphologic measurements involving at least one pupil of an individual 2. More specifically, the pupillary distance may refer to an inter-pupillary distance IPD, a left monocular pupillary distance MPDL and a right monocular pupillary distance MPDR. These parameters are represented in FIG. 1.

The inter-pupillary distance IPD is the distance between the centers of the pupils 3a, 3b of each eye of an individual 2. For simplicity, we will use indistinctly the terms "pupil" and "mirror image of a pupil". Likewise, we will use indistinctly the terms "eye" and "mirror image of an eye".

The monocular pupillary distances MPDL. MPDR, also called half inter-pupillary distances, are commonly defined as the distance between the center of the left pupil 3a, or right pupil 3b respectively and the nasion 7 of the individual 2. The nasion 7 is defined as the middle of the nose at the level of the eyes of the individual 2. The individual 2 presents a sagittal plane which is a vertical plane comprising the perpendicular bisector of the two eyes, where the perpendicular bisector of the eye is defined as the line going through the middle of the segment between the center of rotation of the eyes. In practice, it is also possible to consider the middle of the segment between the two pupils 3a, 3b of the individual 2.

Here, to comply with the 2 dimensions representation of the figure, the sagittal plane is represented by a vertical axis $A_V$ that runs from his/her head to his/her foot and divides the body into left and right parts.

The nasion 7 is located on the vertical axis $A_V$.

As a variation to the common definition of the monocular pupillary distances MPDL, MPDR, the following definition can be used. A spectacle frame 9 to be worn by the individual 2 comprises a bridge 11 and a center 13 of the bridge 11 of the frame 9. Here, the monocular pupillary distances MPDL, MPDR may also be defined as the distance between the center of the left pupil 3a, or right pupil 3b respectively and the center 13 of the bridge 11 of the frame 9.

In this case, the vertical axis $A_V$ is formed by a line that goes through the center 13 of the bridge 11 of the frame 9 and is perpendicular to the boxing line $L_B$ of the frame 9.

The center 13 of the bridge 11 of the frame 9 is considered to be aligned with the nasion 7 on the vertical axis $A_V$.

The method is preferably used by individual 2 who wish to order ophthalmologic equipment online.

To implement the method, the individual 2 may use the system 1 for determining a pupillary distance such as previously described.

Alternatively, the method can also be implemented at an optician shop.

The method for determining pupillary distance is based on processing acquired images of an individual 2 and comprises the following steps that are represented in FIG. 2:

a preliminary step of explaining the method to the individual 2, a step of calibrating an image S10 of the face of the individual 2, a step of acquiring S20 images comprising the following steps:

an optional step of alignment S202 where the individual 2 is instructed to align a mirror image of his/her face with an alignment target displayed on the screen 15, an optional step of recording the spectacle frame S204 of the individual 2, a step of displaying an object S206 on a screen located in front of the individual 2, the displayed object being positioned at a location in front of one eye of the individual 2, a step of instructing S208 the individual 2 to look with at least said eye at said displayed object, a step of acquiring at least an image S210 of a part of the body of the individual 2 including said eye, a step of processing S30 the acquired image comprising the following steps:

a step of determining the location S302 of a plurality of specific features in the acquired image, one of the specific features being a pupil of said eye of the individual 2.

a step of calculating the pupillary distance S304 based on the location of the plurality of specific features.

Several embodiments of this method are described below.

A first possible embodiment is now described.

The method may comprise a preliminary step of explaining the method to the individual 2 so as to better prepare him/her and help him/her to relax (the relax state of the individual 2 being important in order to ensure a natural posture of the body, including of the back of the neck, shoulders and back). During this step of explaining, a description of each steps of the method may for example be displayed on the screen 15 of the individual 2. Thanks to this preliminary step of explaining, the individual 2 is well prepared for the subsequent measurements.

The method comprises a step of calibrating an image S10 of the face of the individual 2. The aim of the step of calibrating an image S10 is to calculate a pixel-to-real-dimension conversion factor of objects (spectacle frame 9, credit card, ruler etc.) in an acquired image. To achieve this calculation, the real dimension and the pixel dimension of the same object are required. In an embodiment the step of calibrating an image S10 may be carried out later in the process.

There are several ways to obtain the real dimension of the objects in an image.

For example, in the case where the individual 2 possesses a given spectacle frame 9, a plurality of geometric parameters related to the spectacle frame 9 can be used to calculate the conversion factor. In a preferred embodiment, the individual 2 provides at least one geometric parameter relative to a dimension of a spectacle frame 9 he/she already possesses, in particular: A size AS, D size DS, L size LS. These dimensions are defined in the norm ISO8624 and are printed on one temple of the frame (as shown in FIG. 3).

In particular, A size AS corresponds to the width of one circle of the frame. D size DS is the length of bridge of the frame, L size LS is the length of the temples.

For example, the individual 2 can type in the geometric parameters in the user interface provided for and displayed on the screen 15 by the computer 4.

According to another example, an image of the printed dimensions can be acquired by the image acquisition unit 6. An Optical Character Recognition (OCR) algorithm is used with the acquired image in order to retrieve the geometric parameters.

In order to obtain the pixel dimension of the same spectacle frame 9 necessary to calculate the conversion factor, the method uses images acquired during the step of acquiring 20 that will later be described in details. According to another example the image acquisition unit 6 is already calibrated to the environment and is able to acquire a direct measurement of the dimension of the frame 9. However, the image acquisition units usually integrated on personal computers and smart devices are not commonly thus calibrated.

According to another example, the image acquisition unit 6 is equipped with 3-dimensions technology and is able to measure the tridimensional position of the face of the individual 2, and more precisely of the pupils of the individual 2.

The geometric parameters can be memorized for later use, for example if the spectacle frame 9 used for the calibration corresponds to a later ordering.

In the case where the individual 2 does not possess a spectacle frame 9, the calibrating of the image S10 can be carried out using other objects of known dimensions such as a credit card or a ruler.

In this case, the image acquisition unit acquires an image of the individual 2 holding the object of known dimension close to his/her eyes. A further step of determining an extent in pixels of said object of known dimension is implemented. The extent of the image of the object of known dimension is then used during the step of calculating a pupillary distance (described below).

The real dimension of the object of known dimension may already be memorized by the calculating unit 8.

Once the real dimension and the pixel dimension of the object are acquired, the computer 4 of the individual 2 transmits them to the server via the telecommunication link 10, and the conversion factor is calculated by the calculating unit 8.

The step of calibrating the image S10 can be carried out at any time of the method.

During the step of acquiring images S20, the individual 2 receives instructions from the server. Said instructions are displayed on the screen 15 in front of the individual 2.

First, the individual 2 is invited to sit comfortably in front of his/her computer 4 (or tablet or smartphone or phablet), more specifically in front of the image acquisition unit 6 which is preferably attached to the screen 15 of the computer 4.

The individual 2 is then instructed to start the acquisition process of the image acquisition unit 6.

In a preferred example, the image acquisition unit 6 acquires a video of the individual 2, i.e. a sequence of images. The images (also called frames) are (each) processed by the calculating unit 8 with an image mirror algorithm in order to obtain mirror images. This image mirror algorithm can be implemented in real time and the resulting mirror video can be displayed in real time by the screen 15.

Alternatively, the image acquisition unit 6 acquires a single image of the individual 2 for each steps of the method.

To facilitate the measurements, the method may comprise an optional step of alignment S202 to help the individual 2 centering his/her face for the measurement.

In this step of alignment S202, the screen is able to provide in real time a mirror image of the image acquired by the acquisition unit 6, along with an alignment target. The alignment target includes for example a predetermined contour that is similar to the contour of an average human face. The alignment target includes for example a substantially oval shape. The individual 2 is instructed to position him/herself so that the image of his/her face displayed on the screen fits inside the alignment target.

Having a well aligned face during the step of image acquisition S20 facilitates the subsequent step of processing S30 the image and reduces the error in calculations.

Moreover, this helps in having the sagittal plane of the head of the individual 2 perpendicular to the acquisition unit 6.

When the sagittal plane of the head of the individual 2 is perpendicular to the acquisition unit 6, the individual 2 is looking straight ahead towards the acquisition unit. The inter-pupillary distance IPD and the monocular pupillary distances MPDL, MPDR are maximized on the image and present realistic dimensions. In the case where the head of the individual 2 is turned, even slightly, towards one side, then the inter-pupillary distance IPD and the monocular pupillary distances MPDL, MPDR present a shorter length on the images than in reality.

In the case where the individual 2 already possesses a spectacle frame 9, an optional step of recording the spectacle frame S204 is performed. This step is illustrated by FIGS. 4a, 4b, 4c.

In this illustration, the individual 2 is not initially wearing his/her spectacle frame 9 (FIG. 4a). The individual 2 is instructed to put his/her spectacle frame 9 on for a short duration (FIG. 4b), for example one second. Said short duration allows the acquisition unit to acquire at least one image of the individual 2 wearing his/her spectacle frame 9.

The individual 2 is then instructed to take the spectacle frame 9 off (FIG. 4c).

The image of the individual 2 wearing the spectacle frame 9 can be used for the calculation of the conversion factor required for the step of calibrating an image S10. Indeed, this image of the spectacle frame 9 provides the pixel dimension of the spectacle frame 9. This pixel dimension of the spectacle frame will be used with the real dimension of the spectacle frame 9 previously retrieved in the step of calibration. Together, the pixel dimension and the real dimension will provide the conversion factor.

In the step of displaying an object S206 on the screen located in front of the individual 2, illustrated by FIG. 5a, an object 17a is displayed on the screen at a location in front of one eye 19a of the individual 2. The one eye can either be the left eye 19a or the right eye 19b of the individual 2. On the example illustrated by FIG. 5a, the method measures the left eye 19a of the individual 2 in the present step, but it possible to measure the right eye 19b first.

In the preferred example, the screen is able to provide a real time display of a mirror image of the individual 2. The object 17a then preferably comprises a real time display of the mirror image of the one eye 19a of the individual 2.

In the step of instructing S208 also illustrated by FIG. 5a, the individual 2 is instructed to look at the mirror image of his/her one eye 19a with at least his/her one eye 19a.

Following our example, the individual 2 looks at the mirror image of his/her left eye 19a, with at least his left eye 19a.

By looking at the mirror image of his/her left eye displayed in front of his/her left eye 19a, the individual 2 simulates looking at infinity with said left eye 19a. The error in the measurement of the left monocular pupillary distance MPDL is greatly reduced.

During this step of instructing S208, the individual 2 is preferably instructed to look at the displayed mirror image of the left eye with both eyes 19a, 19b. It is indeed easier for an individual 2 to proceed in this manner and it helps further reducing the measurement error.

The individual 2 is instructed to look at the mirror image of his left eye 19a for a short duration, for example during one second. This duration is sufficient to implement the method.

The individual 2 is further instructed to stay still in front of the acquisition unit 6 during the step of acquiring at least an image. To achieve accurate measurements, only his/her eyes 19a, 19b should move. Should the individual 2 move during the step of acquiring at least an image, a correction of the measurements may be implemented. This will be described later on.

In the step of acquiring S210 at least an image, the image acquisition unit acquires at least an image, preferably a plurality of images, of a part of the body of the individual 2 including said one eye, here the left eye 19a.

Once the image of the individual 2 is acquired, the individual 2 is instructed to stop the image acquisition. For example the individual 2 is instructed to click on a corresponding button on the user interface. Alternatively the process is automated.

In order to determine the pupillary distances with precision, it is essential that the individual 2 does not move a substantial distance closer or away from the acquisition unit during the step of acquiring S20 images.

As it was described earlier, the determining of the pupillary distances from the acquired image requires the use of a conversion factor. As explained above, this conversion factor is calculated based on the image of the individual 2 wearing a spectacle frame 9 (or holding an object of known dimension). If the individual 2 moves a substantial distance from the image acquisition unit between the capture of the calibration image and the capture of the measurement image, the pixel dimension of the elements in the image changes, and the conversion factor calculated will lead to erroneous calculation of the pupillary distances.

In practice, the difference in distance of the individual 2 to the image acquisition unit 6 between the two sets of measurements should be much shorter than the average inter-pupillary distance IPD, i.e. much shorter than 65 mm, e.g. shorter than 6.5 mm.

The step of processing S30 the acquired image is then carried out.

A first step of determining the location S302 of specific features in the acquired image is carried out. As illustrated by FIG. 6a, one of the specific features comprises the pupil 3a of the mirrored eye 19a of the individual 2.

The pupil 3a can be for example located by the individual 2.

In our example, the screen 15 displays the image of the individual 2 looking at the image of his/her left eye 19a. The individual 2 is then instructed to mark the edges of the left pupil 3a with two sets of cursors 21a, 21b, 23a, 23b. A first set of cursors 21a, 21b is provided to mark the horizontal extent of the image of the pupil. A second set of cursors 23a, 23b is provided to mark the vertical extent of the image of the pupil.

In the case where an image of the individual 2 wearing a spectacle frame has also been acquired, another specific feature includes the frame of the spectacle 9, more precisely the outer edges of the lenses of the spectacle frame 9.

As illustrated by FIG. 7a, the screen 5 displays the image of the individual 2 wearing the frame 9 and the individual 2 is instructed to locate said frame 9. To achieve this, the individual 2 is provided with a third set of cursors 25a, 25b and marks the outer edge of the right lens and the outer edge of the left lens of the spectacle frame 9 with one cursor each.

The distance between the two cursors of the third set of 25a, 25b corresponds to the temple width of the spectacle frame in pixel dimension. As previously it will be used to calculate the conversion factor. This distance is also used to locate the center of the bridge of the spectacle frame 11 (FIG. 7b).

In the case where no image of the individual 2 wearing a spectacle frame has been acquired, another specific feature includes the nasion 7 of the individual 2 (not illustrated).

In another example, the specific features can be determined automatically by an algorithm. In practice, the calculating unit 8 is programmed to identify the image of the pupil and the image of the spectacle frame in the acquired image. This is achieved by state of the art image processing.

In another example, the specific features can be determined by a person remotely connected to the optician server.

In the case where a stream of images has been acquired, the specific features can be located on a plurality of images, either by the individual 2, automatically, or by an operator. An average location of the specific features is then calculated from their locations on each image. This allows reducing the error in the location of the specific features.

In the case when the reference for the measurement of monocular pupillary distance is the center of the bridge of the frame, as the location of the center of the left pupil 3a is retrieved from one image, and the location of the center 13 of the bridge 11 of the spectacle frame 9 is retrieved from another image, the immobility of the individual 2 during the step of acquiring S20 images is of great importance. However, it may be difficult for the individual 2 to stay perfectly still.

That is why to further improve the accuracy of the measurement, the displacement of the individual 2 between two images may be evaluated. For example, the location of a reference feature of the individual 2 in the two images may be tracked. The reference feature includes for example a nostril or a corner of an eye 19a, 19b of the individual 2. The tracking of the reference feature may be done automatically thanks to a tracking algorithm or by an operator.

If the location of the reference feature varies in the images, then the individual 2 was not perfectly still. In this case, it is possible to correct the measurements using the variation in location of the reference feature to improve the accuracy of the measurements.

In the case the nasion is used as a reference (instead of the center of the bridge of the frame as in the previous example), it is also useful to track the position of the nasion from the different images, to be sure that the same point is used as the reference in the different measurements.

Finally, in the step of calculating the pupillary distance S304, a pupillary distance is calculated based on the location of the specific features.

According to our example, the left monocular pupillary distance MPDL is calculated.

For example, the calculating unit 8 determines the position of the center of left pupil 3a of the individual 2 on the image. The position is for instance the address of the pixel corresponding to the center of the left pupil 3a. The address of the pixel corresponding to the center of the left pupil of the individual 2 is calculated based on the position of the two sets of cursors 21a, 21b, 23a, 23b defining the extent of the image of the left pupil.

The other specific feature used for the calculation is for example the center 13 of the bridge 11 of the spectacle frame 9. The address of the pixel corresponding to the center 13 of the bridge 11 of the spectacle frame 9 is calculated based on the position of the third set of cursors 25a, 25b defining the respective outer edges of the lenses of the spectacle frame 9. As illustrated by FIG. 7b, the center 13 of the bridge 11 of the spectacle frame 9 is located at half the width of the frame.

The pixel dimension of the left monocular pupillary distance MPDL is calculated based on the address of the pixel of the center 13 of the bridge 11 of the spectacle frame 9 and on the address of the pixel corresponding to the center of the left pupil 3a of the individual 2.

If necessary, the calculating unit 8 is also able to correct the pixel addresses of the center of the left pupil 3a and of the center 13 of the bridge 11 of the spectacle frame 9 by using the variation in location of the previously mentioned reference features.

The conversion factor previously determined is used to calculate the real dimension of the left monocular pupillary distance MPDL from its pixel dimension.

If no image of the individual 2 wearing a spectacle frame 9 is available, the left monocular pupillary distance MPDL is calculated based on the address of the pixel of the nasion 7 of the individual 2 instead of the address of the pixel of the center 13 of the bridge 11 of the spectacle frame 9.

A pupillary distance measured according to the method of the invention is accurate as the error in measurement is greatly reduced.

In order to determine his/her other monocular pupillary distance (the right monocular pupillary distance MPDR according to the example), some of the steps of the step of acquiring S20 images and of processing said image S30 are repeated for the other eye.

In this case, another object 17b is displayed on the screen 15 at a location in front of the other eye 19b of the individual 2. This other object 17b preferably comprises a real time display of the other eye of the individual 2 (for instance in the frame of displaying a mirror image of the face of the individual 2 as explained above).

The individual 2 is then instructed to look at the other displayed object 17b with his/her other eye 19b. Following our example, the other eye is the right eye 19b, as illustrated by FIG. 5b.

The acquisition unit then acquires at least another image of a part of the body of the individual 2 including said other eye.

For the reason explained earlier, the individual 2 should not move a substantial distance between the set of measurements relative to the left eye 19a, and the set of measurements relative to the right eye 19b. That is why the steps of instructing the individual 2 and acquiring another image, enabling the measurement of the right monocular pupillary distance MPDR are preferably carried out directly after the step of acquiring an image S210 of the left eye 19a, and before the step of processing S30 of the acquired image.

During the step of processing of an image, the images of the left eye 19a looking straight ahead, and the images of the right eye 19b looking straight ahead may be divided into two different sequences. This helps reducing the error in the calculation of the location of the specific features in the images.

The step of processing of an image of the right eye 19b is carried out similarly as for the images of the left eye 19a. FIG. 6b illustrates how two other set of cursors 27a, 27b, 29a, 29b are used to determine the location of the pupil of the other eye and the at least other acquired image.

The calculation of the other monocular pupillary distance MPDR is calculated based on the address of the pixel corresponding to the center of the other pupil of the individual 2 and on the address of the pixel corresponding to one of the other specific feature (for instance the center 13 of the bridge 11 of the frame 9 or the nasion 7 of the individual 2, as explained above), taking into account the conversion factor determined above.

Once both monocular pupillary distances MPDL, MPDR are calculated, the inter-pupillary distance IPD can be obtained by adding them.

The method of determining a pupillary distance IPD, MPDL, MPDR can be followed by a step of fabricating lenses and delivering them to the individual 2. The lenses specifications comprise the inter-pupillary distance IPD and the monocular pupillary distances MPDL, MPDR calculated according to the method. The lenses can be fitted into a spectacle frame chosen by the individual 2 and then delivered to the individual 2.

In a variation of the invention, the objects 17a, 17b displayed on the screen during the step of image acquisition 20 are predetermined shapes. These predetermined shapes are memorized shapes (not represented). The memorized shapes comprise for example two horizontal oval contours that each resemble the shape of an eye.

In the step of displaying the object S206, the predetermined shapes are displayed on the screen 15 at a distance similar to the average inter-pupillary distance IPD. Each of the predetermined shape is thus respectively positioned at a location in front of an eye of the individual 2.

Alternatively, a first approximate inter-pupillary distance of the individual 2 is determined, for example thanks to a facial recognition algorithm. The memorized shapes are then displayed on the screen at a distance similar to the first approximate inter-pupillary distance.

This variation requires the calculating unit 8 to know the size of the pixels of the display screen. This information is easily retrieved with an appropriate algorithm.

In another variation, in the step of instructing S208 the individual 2 is first instructed to look at the object displayed on the screen in front of one of his eye (either a real time display of an image of his/her eye or a memorized shape). The individual 2 is then instructed to pivot his/her head about the vertical axis $A_V$ of his/her body (FIG. 1) while looking at the object displayed in front of his/her eye.

In the step of acquiring S210 at least an image, the acquisition unit acquires a video of the individual 2 when he/she follows the instructions to pivot his/her head.

These steps can be carried out for both eyes of the individual 2.

In the step of processing 30 the acquired image, the specific features are located on a plurality of acquired images. The step of locating S302 of specific features is preferably carried out automatically.

The calculating unit 8 determines a set of values for the monocular pupillary distances MPDL, MPDR and the inter-pupillary distance IPD based on the location of the specific features on the plurality of images.

The calculating unit 8 is then able to retrieve the largest values for the monocular pupillary distances MPDL, MPDR and the inter-pupillary distance IPD from each respective set of values. These largest values correspond to images where the sagittal plane associated to the individual 2 is perpendicular to the acquisition unit.

Thanks to this embodiment of the method, the error in measurement due an incorrect position of the head of the individual 2 is reduced.

Another embodiment of the method is now described.

In a second embodiment, the inter-pupillary distance IPD is calculated directly, without calculating the monocular pupillary distances MPDL, MPDR.

In this embodiment, the individual 2 is instructed to look at an object displayed in front of one eye with his/her one eye and with his/her other eye. The object is preferably a real time display of the mirror image of the face of the individual 2, as explained above in connection with the first embodiment.

FIG. 8*a* illustrates a real time display of the screen in the case where the object is displayed in front of his/her right eye. It is visible on this FIG. 8*a* that the right eye 19*b* looks straight ahead, whereas the left eye 19*a* does not. For emphasis, the left eye 19*a* is represented in a squinting position.

At least an image of the individual 2 looking with his/her one eye and with his/her other eye at the object displayed in front of his/her one eye is acquired. For clarity, this image will be referred to as the first image 31.

The individual 2 is then instructed to look at another object displayed in front of his/her other eye with his/her one eye and with his/her other eye. The object is preferably a real time display of the mirror image of the other eye of the individual 2.

FIG. 8*b* illustrates a real time display of the screen in the case where the object is displayed in front of his/her other eye, the left eye 19*a* to follow the example.

At least another image of the individual 2 looking with his/her other eye at the object displayed in front of his/her other eye is acquired. In this image, the left eye 19*a* is in a straight ahead position and the right eye 19*b* is squinting. For clarity, this image will be referred to as the second image 33.

During the step of processing S30 the images, the individual 2 is provided with sets of cursors (not represented) to determine the location of the center of his/her pupils 3*a*, 3*b*.

On the first image 31, the individual 2 is instructed to locate his/her left pupil 3*a* and his/her right pupil 3*b*. The distance between the respective centers of two pupils IPD1 is calculated based on the pixel addresses of their center.

On the second image 33, the individual 2 is instructed to locate the other position of center of the pupil of his left eye 3*a*'. The calculating unit 8 then calculates the distance between the squinting position and the straight ahead position of the left eye IPD2.

As the calculation is based on the difference between the pixel address of center of the pupil of his left eye 3*a* on the first image 31, and on the pixel address of the other position of the center of the pupil of his left eye 3*a*' on the second image 33, it is important that the individual 2 should not move sideways between the acquisition of the first image 31 and the second image 33.

According to a possible embodiment, the movement of the individual 2 between the first image 31 and the second image 33 may be compensated, for instance by tracking a particular point of the head (such as the nostril or the corner of an eye).

Finally, to obtain the inter-pupillary distance IDP, the calculating unit 8 adds the distance between the two pupils IPD1 and the distance between the squinting position and the straight ahead position of the left eye IPD2.

The invention claimed is:

1. A method for determining at least one pupillary distance of an individual, the method comprising:
   displaying an object on a screen located in front of the individual, the displayed object being positioned at a location in front of one eye of the individual;
   instructing the individual to look with at least said eye at said displayed object;
   acquiring at least an image of a part of the body of the individual including said eye;
   determining the location of a plurality of specific features in the acquired image, one of the specific features being a pupil of said eye of the individual;
   calculating a pupillary distance of the at least one pupillary distance based on the location of the plurality of specific features;
   evaluating a movement of the individual, after acquiring the image;
   displaying another object on the screen at a location in front of the other eye of the individual;
   instructing the individual to look with at least said other eye at said other displayed object;
   acquiring at least another image of a part of the body of the individual including said other eye, after evaluating the movement of the individual;
   determining the location of another pupil of said other eye in the at least other acquired image; and
   calculating another pupillary distance of the at least one pupillary distance based on the location of said other pupil of said other eye.

2. The method for determining the pupillary distance according to claim 1, wherein the pupillary distance is a monocular pupillary distance, and
   wherein the plurality of specific features further includes a specific feature chosen among: an individual spectacle frame and the nasion of the individual.

3. The method for determining the pupillary distance according to claim 2, wherein the acquiring the at least an image and the at least another image is carried out by an image acquisition device attached to the screen.

4. The method for determining the pupillary distance according to claim 1, wherein the pupillary distance is a monocular pupillary distance,
   wherein the plurality of specific features further includes a specific feature chosen among: an individual spectacle frame and the nasion of the individual, and
   wherein the method further comprises calculating an inter-pupillary distance by adding the monocular pupillary distance and the other monocular pupillary distance.

5. The method for determining the pupillary distance according to claim 1, wherein the pupillary distance is an inter-pupillary distance calculated based on the location of the pupil of said one eye and on the location of the pupil of the other eye.

6. The method for determining the pupillary distance according to claim 1, wherein the acquiring the at least an image and the at least another image is carried out by an image acquisition device attached to the screen.

7. The method for determining the pupillary distance according to claim 1, wherein the screen is configured to provide a real-time display of a mirror image of the individual.

8. The method for determining the pupillary distance according to claim 7, further comprising instructing the individual to align the mirror image of a face of the individual with an alignment target displayed on the screen.

9. The method for determining the pupillary distance according to claim 7, wherein the displayed object or the other displayed object comprises a real-time display of one eye or the other eye of the individual.

10. The method for determining the pupillary distance according to claim 1, wherein the specific features or other specific features are automatically located by an algorithm.

11. The method for determining the pupillary distance according to claim 1, further comprising:
acquiring an image of an object of known dimensions placed close to the head of the individual; and
determining an extent of said object of known dimension in the acquired image, said extent being used during the calculating the pupillary distance.

12. A system for determining a pupillary distance of an individual, the system comprising:
a screen configured to display an object at a location in front of one eye of the individual when said screen is located in front of the individual and instructions for the individual to look with said eye at said displayed object, the screen being configured to display another object at a location in front of the other eye of the individual and instructions for the individual to look with at least the other eye at the other displayed object;
an image acquisition device configured to acquire an image of the body of the individual including one eye of the individual and at least another image of a part of the body of the individual including the other eye;
a calculator configured to calculate the pupillary distance of the individual based on the location of specific features located on an acquired image, the specific features include a pupil of said eye of the individual, the calculator being configured to calculate another pupillary distance based on the location of the other pupil of the other eye in the at least other acquired image, the calculator being configured to evaluate a movement of the individual between the image being acquired by the image acquisition device and the other image being acquired by the image acquisition device.

13. The system for determining the pupillary distance according to claim 12, wherein the image acquisition device is attached to the screen.

14. The system for determining the pupillary distance according to claim 12, wherein the calculator is remotely located from the image acquisition device and the screen.

* * * * *